United States Patent [19]

Woods

[11] Patent Number: 4,570,632
[45] Date of Patent: Feb. 18, 1986

[54] CYSTOTOME FOR EYE SURGERY AND METHOD OF OPENING LENS CAPSULE

[76] Inventor: Randall L. Woods, Lee's Summit, Mo.

[21] Appl. No.: 590,447

[22] Filed: Mar. 16, 1984

[51] Int. Cl.[4] ............................................. A61F 17/32
[52] U.S. Cl. .................................... 128/305; 128/751; 433/118
[58] Field of Search ................... 128/305, 751, 303 R; 433/118, 120, 122, 123

[56] References Cited

U.S. PATENT DOCUMENTS

| | | | |
|---|---|---|---|
| 158,863 | 1/1875 | Nichols | 433/120 |
| 215,226 | 5/1879 | Justi | 433/122 |
| 2,129,212 | 9/1938 | Hollenback | 433/120 |

FOREIGN PATENT DOCUMENTS 3022383 12/1981 Fed. Rep. of Germany ... 128/303 R

Primary Examiner—John J. Wilson
Attorney, Agent, or Firm—Schmidt, Johnson, Hovey & Williams

[57] ABSTRACT

A cystotome for producing a continuous series of perforations in the anterior lens capsule of a human eye preparatory to cortex removal in extracapsular cataract extraction has a rectilinearly reciprocable, essentially poniard-shaped cutter for piercing the capsule while it is held taut along the base of an indentation pressed into the capsule such that the cutter moves into and out of a tubular support therefor along a path which is perpendicular to the base of the indentation, the movement of the cystotome along the capsule taking place only while it is out of engagement with the capsule with the cutter fully retracted.

2 Claims, 9 Drawing Figures

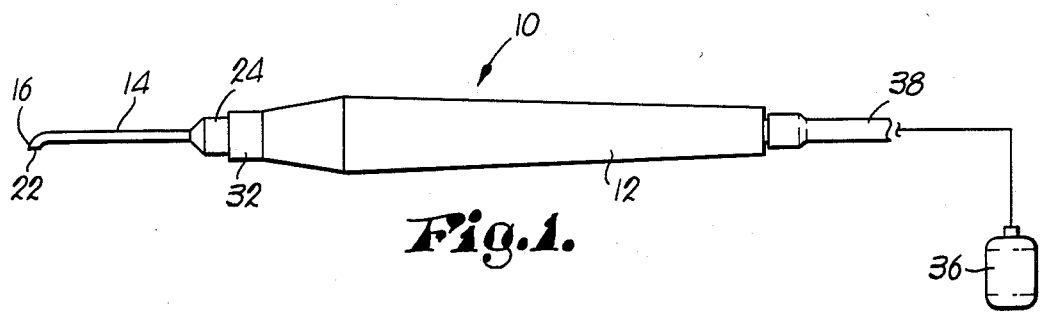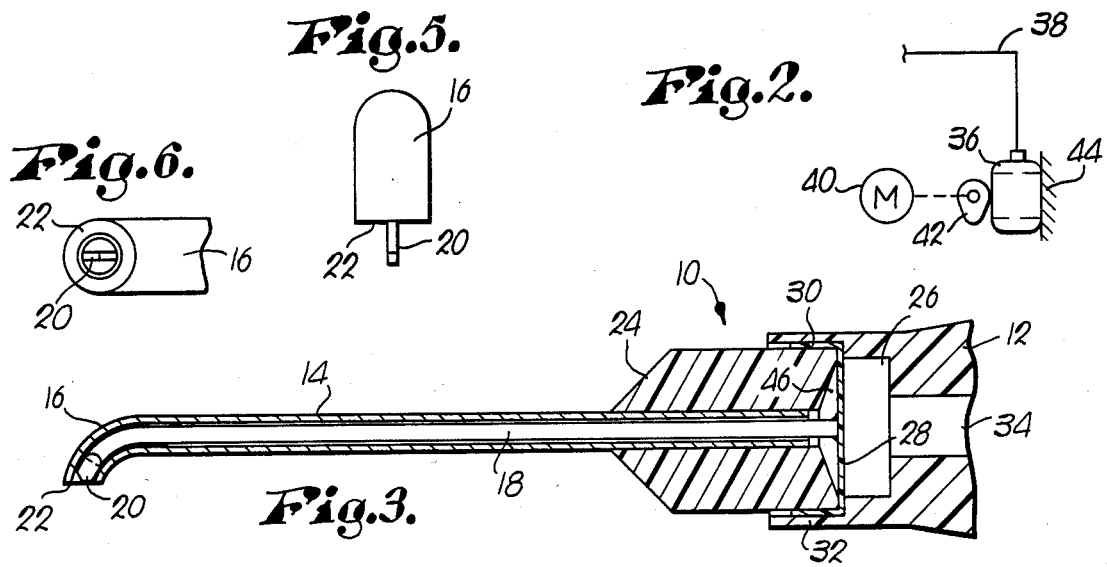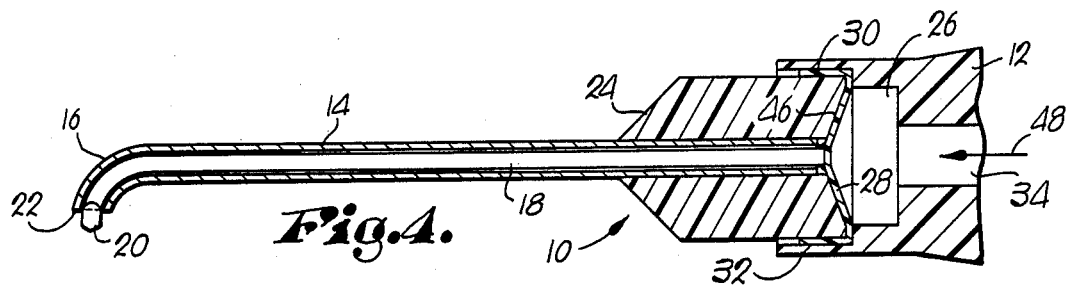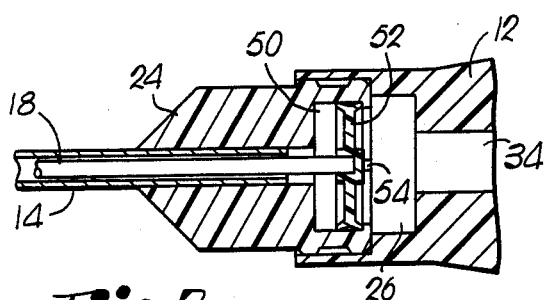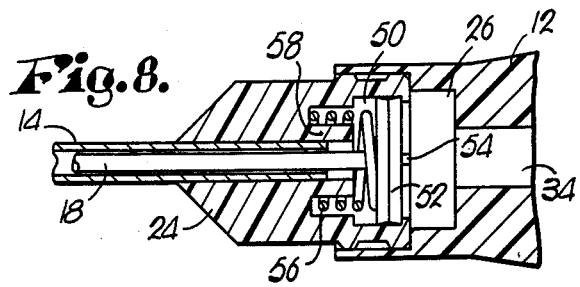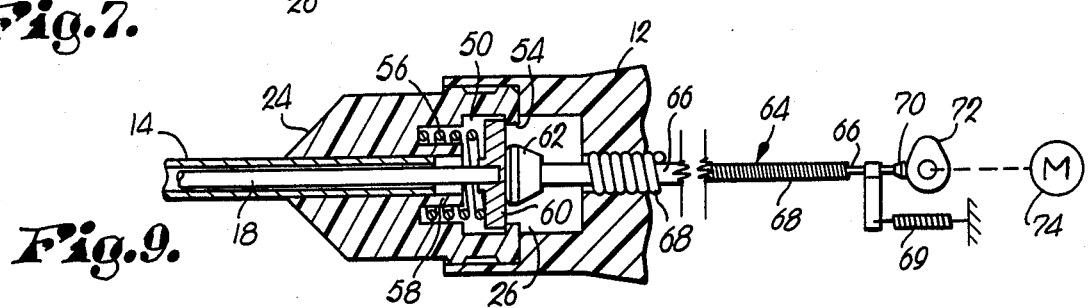

CYSTOTOME FOR EYE SURGERY AND METHOD OF OPENING LENS CAPSULE

In the surgical art of extracapsulary cataract extraction an opening must be provided in the anterior lens capsule of the human eye through which the cataract is removed. The procedure involves inserting a cutting instrument through an access incision in the limbus and thereupon attempting to slice a continuous series of small perforations in the capsule so as to permit removal of the central portion which is surrounded by the perforations. The removal, through use of forceps or other instruments, tears away such capsule portion, fracturing the capsule between the perforations, oftentimes resulting in scattered fragmentation and jagged edges.

While cutting the perforations with such care and precision is idealistic and of extreme importance, the time factor during which the entire cataract surgery must be completed is such that seldom, if ever, is it possible for even the most skilled surgeon to obtain good results. Can opener type instruments, bent-tip needles, hooks and the like in common use usually fail to permit the formation of that kind of opening which will allow easy removal of the cortex, especially in difficult to reach areas without first pulling out flaps of anterior capsule along the opening and cutting the flaps away with suitable scissors.

In accordance with the concepts of my invention presently existing problems are solved by provision of a cystotome which produces proper perforations, strategically located and distinctly spaced within the shortened time frame required for such initial step in the cataract operation. No longer is it necessary for the surgeon to hurriedly carve away on the capsule in absence of imprecision until, in one way or another, some type of hole is presented which will permit him to quickly proceed in an attempt to extract as much of the cortex as possible.

Instead, I provide a cutter much in the nature of a tiny poniard, dirk or dagger having a triangular configuration provided with a pair of opposed, keenly sharpened edges which converge toward a needle-like point which gently pierces the capsule prior to cutting of the perforation by the sharp edges.

Additionally, I provide a flat surface on the extremity of the tool which is initially brought to bear on the capsule such as to form a small indentation through which the cutter is extended. As a consequence, the cutter, which reciprocates rectilinearly, passes through the capsule perpendicularly to the base of the indentation. Moreover, after each cutting step, the cutter is fully retracted before the cystotome is lifted off the capsule and moved to the next indentation-producing step.

The result is the rapid formation of a continuous series of sharply defined, separate perforations absent fragmentation, tearing, flap formations, jagged edges and bruising of tissues, all with substantial ease and high precision.

In the drawing:

FIG. 1 is a side elevational view of one embodiment of a cystotome for eye surgery made according to my present invention capable of carrying out the method of the invention for opening the lens capsule of a human eye;

FIG. 2 is a schematic view of power means for actuating the squeeze container shown in FIG. 1;

FIG. 3 is an enlarged, fragmentary, longitudinal, cross-sectional view of the cystotome of FIG. 1 showing the cutter retraction;

FIG. 4 is a view similar to FIG. 3 showing the cutter extended;

FIG. 5 is an enlarged, fragmentary view showing the outer end of the cutter of my cystotome;

FIG. 6 is a view, enlarged over FIG. 6, showing one end of the cystotome with the cutter extended;

FIG. 7 is a view similar to FIG. 3 showing a modified form of cutter shaft actuator;

FIG. 8 is a view similar to FIG. 7 showing another modified form of my present invention; and FIG. 9 is a view similar to FIGS. 3, 7 and 8 showing still another form of the present invention.

With reference to FIGS. 1 and 3–6, a cystosome 10 includes an elongated handle 12, an elongated tube 14 provided with a preferably curved, lateral extension 16 at its outermost end, a flexible shaft 18 in the tube 14 and a cutter 20 on the outer end of the shaft 18. The extension 16 terminates in a continuous, annular, flat, outermost surface 22 which is desirably parallel with the longitudinal axes of the tube 14 and the shaft 18, and the somewhat pointed cutter 20 may be sharpened and be formed by flattening a portion of the shaft 18. The shaft 18 is reciprocable along its longitudinal axis and cutter 20 is disposed for relatively short, repetitive strokes into the extension 16 (FIGS. 3 and 6) and out of the extension 16 beyond the surface 22 (FIGS. 4 and 5) during reciprocation of the shaft 18.

The inner end of the tube 14 is surrounded by and secured to an enlargement 24 which is, in turn, releasably attached to the inner end of the handle 12. The handle 12 is in the nature of a housing having a cavity 26 closed by a diaphragm 28 secured to the shaft 18 and closing the proximal end of the enlargement 24. The relatively thin, vibratory, dividing membrane forming the diaphragm 28 has a wrapping 10 around the enlargement 24 held in place by a collar 32 integral with the handle 12 and surrounding the wrapping 30 in relatively tight, frictional engagement therewith, holding the diaphragm normally taut as shown in FIG. 3. The handle 12 has a longitudinal bore 34 communicating with the cavity 26.

A squeeze bottle or other flexible container 36 for fluid, such as air, capable of pressurizing the cavity 26, has a conduit 38 releasably connected to the handle 12 in communication with the bore 34. In lieu of hand squeezing of the container 36, it may be power squeezed (FIG. 2) by a motor 40, rotating a cam 42 for periodically pressing the container 36 against an anvil 44 or the like. The enlargement 24 has a frustoconical recess 46 for accommodating the diaphragm 28 when fluid pressure is directed into the cavity from the container 36 as shown by an arrow 48 in FIG. 4.

In FIG. 7, the enlargement 24 has a cylindrical recess 50 receiving a piston 52 secured to the shaft 18. As the piston 52 is reciprocated during use of the container 36, the extent of retraction of the cutter 20 into the extension 16 is limited by a series of piston stops 54 extending radially into the recess 50. In FIG. 8, a spring 56 is coiled about the shaft 18 in the recess 50 for assisting in the retraction of the cutter 20. The spring 56 abuts the piston 52 and encircles a guide 58 therefor formed in the enlargement 24.

In lieu of the diaphragm 28 or the piston 52, a disc 60 (shown in FIG. 9) is secured to the shaft 18 for reciprocation along the recess 50, yieldably restrained by the spring 56. A plunger 62 in the cavity 26 is employed in conjunction with a so-called Bowden cable 64 having a wire 66 made of spring steel and enclosed in a helical cable 68 for transmitting motions along corners and curves. One end of the cable 68 is secured to the enlargement 24 and the inner end of the wire 66 is secured to the plunger 62. The wire 66 is spring loaded at 69 to yieldably maintain a follower 70 on the wire 66 in engagement with a cam 72. A motor 74 rotates the cam 72 in a manner similar to the relationship between the motor 40 and the cam 42 in FIG. 2.

OPERATION

As an initial step in extracapsular cataract extraction, a small incision is made at or near the limbus, border or edge of the eye just large enough to permit insertion of the tube 14 until the surgeon is able to place the surface 20 flatly against the anterior lens capsule with but light pressure sufficient only to deform the capsule, producing a small indentation in the capsule conforming in shape and size with the outermost, free end of the extension 16. Such indentation will have a flat base engaged by and parallel with the flat surface 22.

Thereupon, the cutter is caused to move from its position shown in FIG. 3 (confined within the extension 16) to the position shown in FIG. 4 (projected outwardly beyond the surface 22). The cutter 20 moves, therefore, in perpendicular relationship to the base of the indentation, forming a small perforation in the capsule.

In addition to such perpendicular movement of the cutter 20, it is also extremely important to note that, at this juncture, the cutter is retracted out of the perforation along the same path, back into the extension 16, as shown in FIG. 3, before the surface 22 is raised off the capsule such as to provide a clean, smooth cut free of rough, jagged or torn edges.

To accomplish such highly desirable results, care must be exercised in the forming and sharpening of the cutter 20. It dare not be hook-like for the reason that the can opener techniques heretofore practiced must be avoided. Instead of cutting and slicing as, for example, when using conventional knives, scissors and other blades, my improvements contemplate very short, quick, stabbing or piercing actions comparable to thrusting a dagger, needle or other pointed weapon into a body and quickly removing the instrument with truly rectilinear, reciprocable movements. The penetration is quite shallow but must be performed as a cutting action rather than by merely forcing the cutter 20 through the tissue causing it to break away as by puncturing.

Hence the cutter 20 may be sharp-pointed and triangular (as in a poniard), keenly sharpened along both edges which converge toward its pointed end. The tapering must be such that the cutter 20 is very small and keen at its outer extremity.

The next successive perforation is formed after the cutter 20 is fully retracted and such must take place before the surface 22 is raised off the capsule. The extension 16 is then moved to a new position and the surface 22 again pressed against the capsule ready for making the next perforation. This avoids all undesired tearing or cutting of the capsule between the perforations, entirely unlike can opener, hooking and other practices heretofore known in this specialized art. The procedure is continued until a continuous series of peripheral perforations is produced. The loose central area of the capsule may then be removed by pulling it out with a long blade forceps or other instrument, leaving an essentially smooth edged opening through which the cataract is extracted.

Manifestly any selected one of the above described mechanisms may be employed for the purpose of effecting reciprocation of the cutter 20 out of and back into the extension 16. Also, it is not absolutely essential that the cuts be in the form of radial slits. The openings may be punched to produce perforations through use of conical cutters or cutters of other configurations, although cutter 20 as herein shown and described is to be preferred.

I claim:

1. In the surgical art of extracapsular cataract extraction, a cystotome for incising a continuous series of perforations in the anterior lens capsule of a human eye preparatory to removal of a portion of said anterior lens capsule within the confines of said perforations to provide a cataract clearance opening in said anterior lens capsule, said cystotome comprising:
   an elongated tube having a lateral extension at one end thereof terminating in a flat, continuous, outermost surface adapted to be held by the surgeon flatly against said anterior lens capsule;
   a flexible shaft in said tube and reciprocable along the longitudinal axis thereof;
   a cutter on one end of the shaft and disposed for relatively short, repetitive strokes into and out of the extension beyond said surface during reciprocation of said shaft;
   means for reciprocating the shaft,
   said cutter being a relatively short, essentially poniard-shaped, triangular instrument having keenly sharpened edges coverging toward an outermost, sharp point for stabbing the capsule to present a smooth, sharp slice in absence of tearing.

2. The invention of claim 1, said extension confining the cutter to rectilinear reciprocation into and out of the extension.

* * * * *